US011366304B2

(12) United States Patent
Nakagawa et al.

(10) Patent No.: US 11,366,304 B2
(45) Date of Patent: Jun. 21, 2022

(54) OPTICAL MODULE FOR ENDOSCOPE, ENDOSCOPE, AND MANUFACTURING METHOD OF OPTICAL MODULE FOR ENDOSCOPE

(71) Applicant: OLYMPUS CORPORATION, Tokyo (JP)

(72) Inventors: Yusuke Nakagawa, Nagano (JP); Youhei Sakai, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 89 days.

(21) Appl. No.: 17/076,185

(22) Filed: Oct. 21, 2020

(65) Prior Publication Data

US 2021/0116696 A1 Apr. 22, 2021

Related U.S. Application Data

(63) Continuation of application No. PCT/JP2019/017951, filed on Apr. 26, 2019.

(30) Foreign Application Priority Data

Apr. 26, 2018 (WO) .................. PCT/JP2018/017101
Dec. 6, 2018 (WO) .................. PCT/JP2018/044981

(51) Int. Cl.
*G02B 23/24* (2006.01)

(52) U.S. Cl.
CPC ..... *G02B 23/2423* (2013.01); *G02B 23/2469* (2013.01); *G02B 23/2476* (2013.01)

(58) Field of Classification Search
CPC ............ G02B 23/2423; G02B 23/2469; G02B 23/2476
See application file for complete search history.

(56) References Cited

U.S. PATENT DOCUMENTS 5,625,730 A * 4/1997 Ishikawa ............... G02B 6/3885
                                                         385/98
6,282,350 B1 * 8/2001 Takahashi ............. G02B 6/4243
                                                         385/94

(Continued)

FOREIGN PATENT DOCUMENTS

EP       0 943 941 A1    9/1999
JP       62-31811 A      2/1987

(Continued)

OTHER PUBLICATIONS

International Search Report dated Jul. 16, 2019 received in International Application No. PCT/JP2019/017951, together with an English-language translation.

(Continued)

*Primary Examiner* — Rowina J Cattungal
(74) *Attorney, Agent, or Firm* — Scully, Scott, Murphy & Presser, P.C.

(57) ABSTRACT

An optical module for endoscope includes an optical element, an optical fiber, a ferrule including a first principal surface, a second principal surface, and a side surface, an opening of an insertion hole being present on the first principal surface, the insertion hole having a bottom surface made of a transparent material, the optical fiber being inserted into the insertion hole, the optical element being bonded to the second principal surface, an opening of a groove connected to the insertion hole being present on the first principal surface, the grove having a bottom surface made of the transparent material, and transparent resin disposed in the insertion hole and the groove of the ferrule.

9 Claims, 10 Drawing Sheets

(56) References Cited

U.S. PATENT DOCUMENTS

| | | | |
|---|---|---|---|
| 6,304,708 B1 | 10/2001 | Fukuyama et al. | |
| 6,485,197 B1* | 11/2002 | Kato | G02B 6/4248 385/94 |
| 2003/0142921 A1 | 7/2003 | Dallas et al. | |
| 2003/0179993 A1 | 9/2003 | Shigenaga et al. | |
| 2006/0039658 A1* | 2/2006 | Furuyama | G02B 6/43 385/88 |
| 2007/0217741 A1 | 9/2007 | Shigenaga et al. | |
| 2011/0194820 A1* | 8/2011 | Sakurai | G02B 6/4202 385/88 |
| 2014/0286363 A1* | 9/2014 | Kasai | B23K 1/0008 228/101 |
| 2015/0342530 A1 | 12/2015 | Dekker et al. | |
| 2016/0079728 A1* | 3/2016 | Matsuyama | G02B 6/3616 385/137 |
| 2018/0008123 A1 | 1/2018 | Iwaisako | |
| 2018/0055342 A1 | 3/2018 | Sakai et al. | |
| 2018/0145789 A1 | 5/2018 | Iwasaki et al. | |

FOREIGN PATENT DOCUMENTS

| | | |
|---|---|---|
| JP | 11-326704 A | 11/1999 |
| JP | 2004-4432 A | 1/2004 |
| JP | 2013-64846 A | 4/2013 |
| JP | 2015-14646 A | 1/2015 |
| JP | 2015-524285 A | 8/2015 |
| JP | 2018-81255 A | 5/2018 |
| WO | 2014/006536 A2 | 1/2014 |
| WO | 2014/168187 A1 | 10/2014 |
| WO | 2016/157301 A1 | 10/2016 |
| WO | 2016/185537 A1 | 11/2016 |
| WO | 2017/141369 A1 | 8/2017 |

OTHER PUBLICATIONS

International Search Report dated Feb. 26, 2019 received in International Application No. PCT/JP2018/044981.

International Search Report dated Jul. 31, 2018 received in International Application No. PCT/JP2018/017101.

\* cited by examiner

OPTICAL MODULE FOR ENDOSCOPE, ENDOSCOPE, AND MANUFACTURING METHOD OF OPTICAL MODULE FOR ENDOSCOPE

CROSS REFERENCE TO RELATED APPLICATION

This application is a continuation application of PCT/JP2019/017951 filed on Apr. 26, 2019 and claims benefit of International Application No. PCT/JP2018/017101 filed on Apr. 26, 2018 and International Application No. PCT/JP2018/044981 filed on Dec. 6, 2018, the entire contents of which are incorporated herein by this reference.

BACKGROUND OF THE INVENTION

1. Field of the Invention

The present invention relates to an optical module for endoscope including a fiber holding section in which an insertion hole into which an optical fiber is inserted and fixed by transparent resin is present, an endoscope including the optical module for endoscope in which the insertion hole into which the optical fiber is inserted and fixed by the transparent resin is present, and a manufacturing method of the optical module for endoscope in which the insertion hole into which the optical fiber is inserted and fixed by the transparent resin is present.

2. Description of the Related Art

An endoscope includes an image pickup device at a distal end portion of an elongated insertion section. In recent years, in order to display a high-quality image, an image pickup device with a large number of pixels has been examined. When the image pickup device with the large number of pixels is used, an image signal amount transmitted from the image pickup device to a signal processing apparatus (a processor) increases. Accordingly, in electric signal transmission through a metal wire by an electric signal, it is necessary to increase a wire diameter of the metal wire or use a plurality of metal wires in order to transmit a necessary signal amount. It is likely that an insertion section for a wire increases in diameter.

To reduce the diameter of the insertion section and make the insertion section less invasive, optical signal transmission through a thin optical fiber by an optical signal instead of the electric signal is preferable. For the optical signal transmission, an optical module of an E/O type (an electrical to optical converter) that converts an electric signal into an optical signal and an optical module of an O/E type (an optical to electrical converter) that converts an optical signal into an electric signal are used.

For the reduction of the diameter of the insertion section of the endoscope, a reduction in the size of an optical module is important.

International Publication No. 2016/157301 discloses an optical module for endoscope in which an injection hole into which resin is injected is present in a ferrule in which an insertion hole into which an optical fiber is inserted and fixed using resin is present.

SUMMARY OF THE INVENTION

An optical module for endoscope in an embodiment includes: at least one optical element including a light emission circuit that outputs an optical signal or a light reception circuit to which the optical signal is inputted and an external electrode connected to the light emission circuit or the light reception circuit; at least one optical fiber for transmitting the optical signal; a ferrule including a first principal surface, a second principal surface on an opposite side of the first principal surface, and a side surface orthogonal to the first principal surface, an opening of at least one insertion hole being present on the first principal surface, the insertion hole having a bottom surface made of a transparent material, the optical fiber being inserted into the insertion hole, the external electrode of the optical element being bonded to a bonding electrode of the second principal surface, an opening of a groove connected to the insertion hole being present on the first principal surface, the groove having a bottom surface made of the transparent material; and transparent resin of an ultraviolet curing type or an ultraviolet and thermosetting type disposed in the insertion hole and the groove of the ferrule.

An endoscope in an embodiment includes an optical module for endoscope, the optical module for endoscope including: at least one optical element including a light emission circuit that outputs an optical signal or a light reception circuit to which the optical signal is inputted and an external electrode connected to the light emission circuit or the light reception circuit; at least one optical fiber for transmitting the optical signal; a ferrule including a first principal surface, a second principal surface on an opposite side of the first principal surface, and a side surface orthogonal to the first principal surface, an opening of at least one insertion hole being present on the first principal surface, the insertion hole having a bottom surface made of a transparent material, the optical fiber being inserted into the insertion hole, the external electrode of the optical element being bonded to a bonding electrode of the second principal surface, an opening of a groove connected to the insertion hole being present on the first principal surface, the groove having a bottom surface made of the transparent material; and transparent resin of an ultraviolet curing type or an ultraviolet and thermosetting type disposed in the insertion hole and the groove of the ferrule.

A manufacturing method of an optical module for endoscope in an embodiment includes: manufacturing a ferrule including a first principal surface, a second principal surface on an opposite side of the first principal surface, and a side surface orthogonal to the first principal surface, an opening of an insertion hole being present on the first principal surface, the insertion hole having a bottom surface made of a transparent material, an opening of a groove connected to the insertion hole being present on the first principal surface, the groove having a bottom surface made of the transparent material; bonding, to a bonding electrode on the second principal surface of the ferrule, an external electrode of an optical element including a light emission circuit or a light reception circuit and the external electrode connected to the light emission circuit or the light reception circuit; inserting an optical fiber for transmitting an optical signal into the insertion hole of the ferrule; injecting the transparent resin not hardened yet into the groove and disposing the unhardened transparent resin in the groove and the insertion hole; and hardening the transparent resin with ultraviolet ray irradiation or the ultraviolet ray irradiation and heating.

DETAILED DESCRIPTION OF THE PREFERRED EMBODIMENTS

First Embodiment

Figure 1:
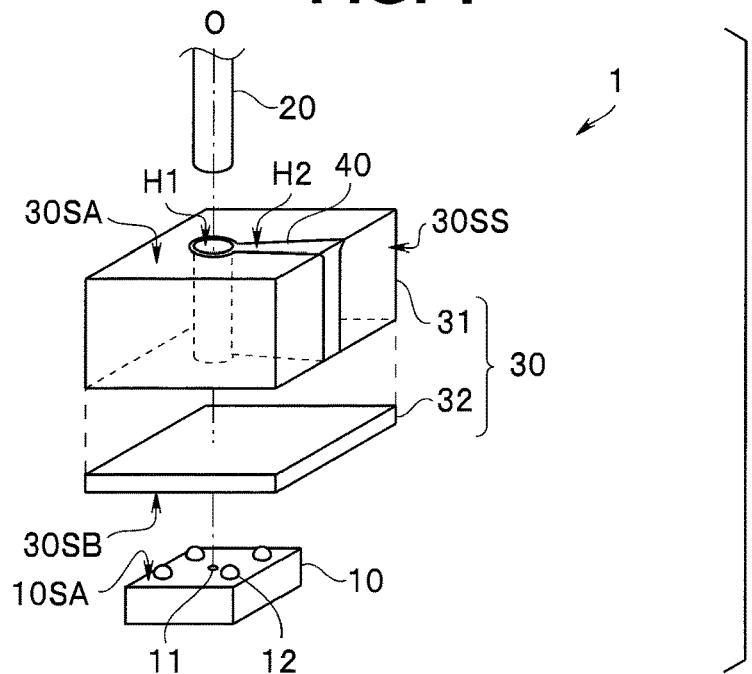
FIG. 1 is an exploded perspective view of an optical module in a first embodiment.

An optical module for endoscope 1 (hereinafter referred to as "optical module 1") in a first embodiment is explained with reference to FIG. 1 to FIG. 3. Note that, in the following explanation, drawings based on respective embodiments are schematic views. It should be noted that relations between thicknesses and widths of respective portions, ratios of the thicknesses of the respective portions, and the like are different from actual ones. Portions, relations and ratios of dimensions of which are different, are sometimes included among the drawings. Illustration of and imparting of reference numerals and signs to a part of components are sometimes omitted.

Figure 22:
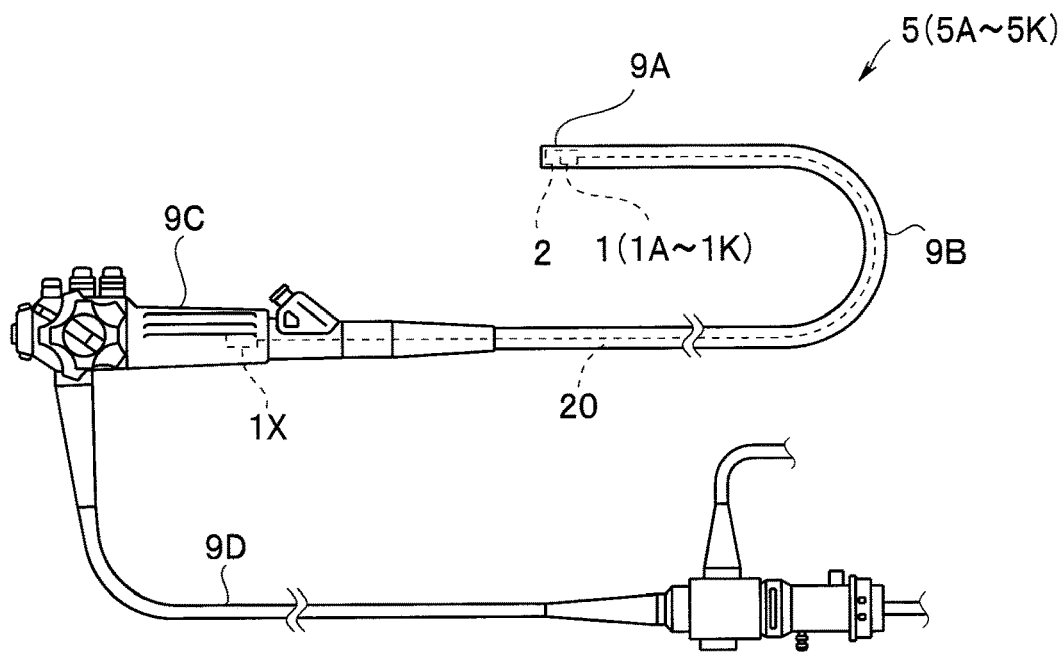
FIG. 22 is a schematic view of an endoscope in a third embodiment.

The optical module 1 is an ultrasmall E/O type module (an electrical to optical converter) that converts an electric signal outputted by an image pickup device 2 of an endoscope 5 into an optical signal and transmits the optical signal (see FIG. 22).

The optical module 1 includes an optical element 10, an optical fiber 20, and a fiber holding section (a ferrule) 30.

The optical element 10 is a VCSEL (vertical cavity surface emitting laser) including a light emitting section 11 that outputs an optical signal. The ultrasmall optical element 10, a plan view dimension of which is 235 μm×235 μm, includes, on a light emission surface 10SA, the light emitting section 11 that has a diameter of 10 μm and outputs an optical signal and four external electrodes 12 that have a diameter of 70 μm and are connected to the light emitting section 11. Note that two of the four external electrodes 12 are dummy electrodes.

The optical fiber 20 that transmits an optical signal includes, for example, a core having a diameter of 62.5 μm and a clad having a diameter of 80 μm and covering an outer circumference of the core.

The fiber holding section 30 includes a first principal surface 30SA, a second principal surface 30SB opposed to the first principal surface 30SA, and a side surface 30SS orthogonal to the first principal surface 30SA. The fiber holding section 30 is a bonded substrate of a silicon substrate 31 configuring the first principal surface 30SA and a glass substrate 32 configuring the second principal surface 30SB. Note that a direction in which the silicon substrate 31 of the fiber holding section 30 is disposed is sometimes referred to as "upper" and a direction in which the glass substrate 32 is disposed is sometimes referred to as "lower".

Figure 2:
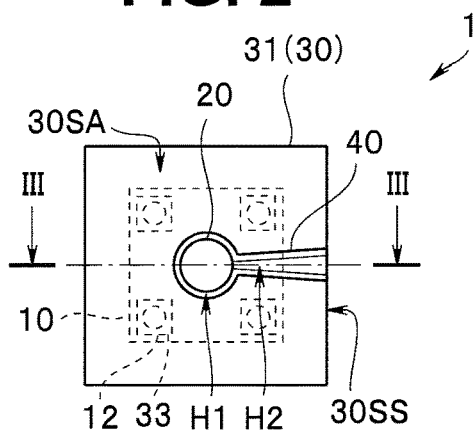
FIG. 2 is a top view of the optical module in the first embodiment.
Figure 3:
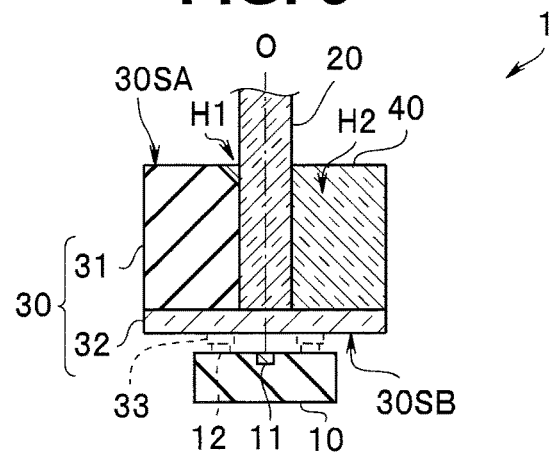
FIG. 3 is a sectional view taken along a line of FIG. 2.

In the top view shown in FIG. 2, the fiber holding section 30 is an ultrasmall type having a horizontal width of 1 mm and a vertical width of 0.5 mm.

A bonding electrode 33 is disposed on the second principal surface 30SB, that is, the glass substrate 32 of the fiber holding section 30. The external electrode 12 of the optical element 10 is bonded to the bonding electrode 33. The bonding electrode 33 is connected to a not-shown wire for transmitting a driving signal.

An opening (an insertion hole opening) of an insertion hole H1, into which the optical fiber 20 is inserted, is present on the first principal surface 30SA of the fiber holding section 30. Since the insertion hole H1 pierces through the silicon substrate 31, a wall surface of the insertion hole H1 is formed of silicon. However, the insertion hole H1 is bottomed and a bottom surface (an insertion hole bottom surface) of the insertion hole H1 is formed of the glass substrate 32, which is a transparent material. An inner diameter of the bottom surface of the insertion hole H1 is slightly larger than an outer diameter of the optical fiber 20, for example, 85 μm.

Since the insertion hole H1 is present in a position opposed to the light emitting section 11 of the optical element 10, a center axis of the optical fiber 20 inserted into the insertion hole H1 coincides with an optical axis O of the optical element 10. The optical fiber 20 is optically coupled to the optical element 10.

An opening (a groove opening) of a groove (a slit or a path) H2 extended from the insertion hole H1 is present on the first principal surface 30SA of the fiber holding section 30. The groove H2 is extended to the side surface 30SS of the fiber holding section 30. The groove H2 includes an opening on the side surface 30SS (a side surface opening) as well. A width of the groove H2 decreases from the side surface 30SS toward the insertion hole H1. In other words, the width of the groove H2 is the narrowest in a connecting section to the insertion hole H1. Since the groove H2 pierces through the silicon substrate 31, a wall surface of the groove H2 is formed of silicon. However, the groove H2 is bottomed. A bottom surface (a groove bottom surface) of the groove H2 is formed of the glass substrate 32, which is the transparent material.

For example, when an inner diameter of the bottom surface of the insertion hole H1 is 85 μm, a width of the bottom surface of the groove is 50 μm in the side surface opening and is 30 μm in the connecting section to the insertion hole H1. The width of the connecting section of the groove H2 to the insertion hole H1 only has to be smaller than an inner diameter of the insertion hole H1 but is preferably 80% or less of the inner diameter of the insertion hole H1 in order to stably hold the optical fiber 20 inserted into the insertion hole H1.

Note that the insertion hole H1 and the groove H2 have tapers. In other words, the insertion hole opening is larger than the insertion hole bottom surface and the groove opening is larger than the groove bottom surface. For example, when the inner diameter of the insertion hole bottom surface is 85 μm and the width of the groove bottom surface is 50 μm, the inner diameter of the insertion hole opening is 120 μm and the width of the groove opening is 90 μm.

As explained above, the optical fiber 20 is fixed by transparent resin 40 of an ultraviolet curing type injected from the groove H2. Accordingly, the transparent resin 40 is disposed in the insertion hole H1 and the groove H2. Note that the transparent resin 40 disposed in the insertion hole H1 is not illustrated because the transparent resin 40 is disposed in a small gap between an outer surface of the optical fiber 20 and the wall surface of the insertion hole H1.

In an ultrasmall optical module, work for fixing an optical fiber to a fiber holding section (a ferrule) with an adhesive is not easy. In other words, it is not easy to irradiate an ultraviolet ray for hardening on the transparent resin 40 disposed in the gap between the optical fiber 20 and the insertion hole H1. When the hardening of the transparent resin 40 is insufficient, the fixing of the optical fiber is insufficient, and it is likely that reliability of the optical module is deteriorated. Transmission efficiency is deteriorated if air bubbles remain when the unhardened transparent resin 40 is injected into the insertion hole H1, Not only the opening of the insertion hole H1 but also the opening of the groove H2 is present on the first principal surface 30SA of the fiber holding section 30 of the optical module 1. Accordingly, an ultraviolet ray irradiated from at least one of the first principal surface 30SA and the side surface 30SS passes through the transparent resin 40 disposed in the groove H2 to thereby reach the transparent resin 40 in the insertion hole H1. Accordingly, the transparent resin 40 in the insertion hole H1 for fixing the optical fiber 20 can be sufficiently hardened. Further, since the transparent resin 40 flows into the insertion hole H1 by passing through the groove H2, air bubbles do not remain in the transparent resin 40.

Note that, as explained below, in the fiber holding section 30, the groove H2 is absent in an opposed region opposed to a region where the bonding electrode 33 is disposed. Accordingly, it is unlikely that the thin glass substrate 32 is broken during bonding of the optical element 10.

The optical module 1 has high reliability and is small in size and has high transmission efficiency and is easily manufactured.

<Manufacturing Method of the Optical Module for Endoscope>

Figure 4:
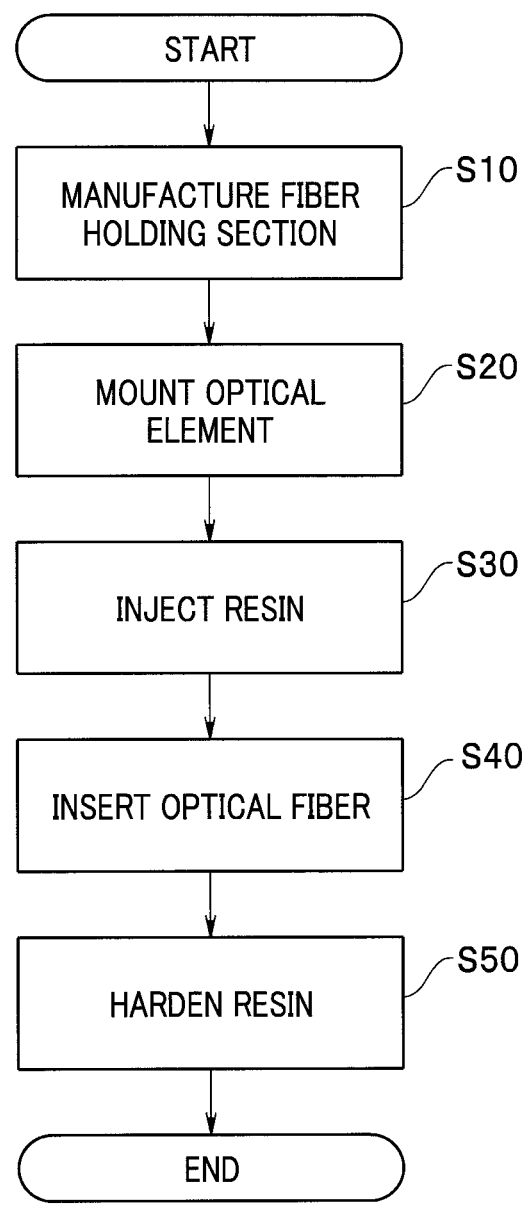
FIG. 4 is a manufacturing flowchart of the optical module in the first embodiment.

A manufacturing method of the optical module 1 is explained according to a flowchart of FIG. 4.

<Step S10> Fiber Holding Section Manufacturing Process

The insertion hole H1, the groove H2, and the like are formed in a bonded wafer obtained by, for example, anodically bonding a silicon wafer and a glass wafer and then are cut, whereby the fiber holding section 30 formed by the silicon substrate 31 and the glass substrate 32 is manufactured.

Note that an external shape of the fiber holding section 30 is a rectangular parallelepiped but may be a column or a columnar prism.

The insertion hole H1 and the groove H2 are formed by etching of the bonded wafer. For example, the insertion hole H1 or the like, a wall surface of which is substantially perpendicular to a principal surface thereof, can be accurately and easily formed by reactive ion etching (RIE). Since the glass wafer functions as an etching stop layer, the insertion hole H1 or the like including glass as the bottom surface is formed.

The insertion hole H1 or the like may be formed by wet etching. A shape of the insertion hole H1 may be a prism besides a column if the optical fiber 20 can be held by the inner surface of the insertion hole H1.

Figure 5:
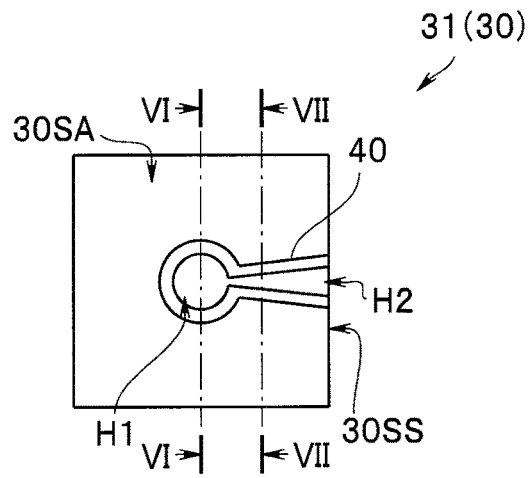
FIG. 5 is a top view of a fiber holding section of the optical module in the first embodiment.
Figure 6:
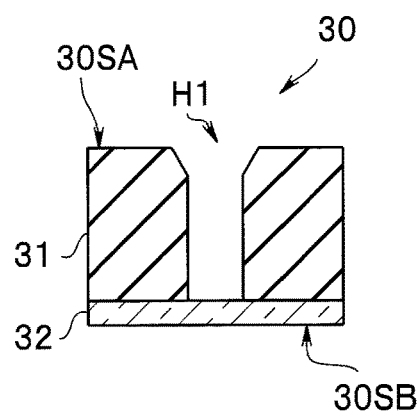
FIG. 6 is a sectional view taken along a line VI-VI of FIG. 5.
Figure 7:
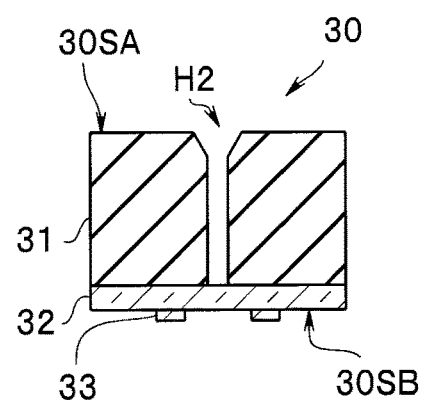
FIG. 7 is a sectional view taken along a line VII-VII of FIG. 5.

As shown in FIG. 5 to FIG. 7, the insertion hole H1 and the groove H2 of the fiber holding section 30 have tapers in the openings. The tapers of the insertion hole H1 and the groove H2 are formed by performing anisotropic dry etching and thereafter performing isotropic dry etching. The tapers are not essential elements of the insertion hole H1 and the groove H2. However, insertion of the optical fiber 20 and injection of the transparent resin 40 into the insertion hole H1 and the groove H2 having the tapers are easy.

Note that transmission efficiency is deteriorated when a thickness of the glass substrate 32 is large. Accordingly, the glass wafer of the bonded wafer is thinned to a thickness larger than 5 μm and smaller than 50 μm.

In other words, if the thickness of the glass substrate 32 is smaller than 50 μm, since light having a wavelength of an optical signal is transmitted 95% or more, the transmission efficiency is high. Note that if the thickness of the glass substrate 32 is larger than 5 μm, the glass substrate 32 is less easily broken in later processes.

Note that a thickness of the silicon substrate 31 is preferably larger than 100 μm in order to stably hold the optical fiber 20.

In the bonded wafer, after the insertion hole H1 and the groove H2 are formed on the first principal surface 30SA, the glass wafer is thinned and the bonding electrode 33 and the like are disposed on the second principal surface 30SB. A plurality of fiber holding sections 30 are manufactured by cutting the bonded wafer.

Note that the fiber holding section may be manufactured by machining of an SOI wafer. In other words, in an SOI wafer formed by a first silicon layer/a silicon oxide layer/a second silicon layer, the insertion hole H1 and the groove H2 are formed in the first silicon layer using the silicon oxide layer as an etching stop layer. The bottom surfaces of the insertion hole H1 and the like are the silicon oxide layer. A through-hole functioning as an optical path is formed in the second silicon layer. Note that the second silicon layer may be removed. When an optical signal is infrared light, since silicon is substantially a transparent material for the infrared light, the transmission efficiency is not deteriorated even if the second silicon layer is present in the optical path. The fiber holding section may be manufactured by machining of a silicon substrate, on one surface of which the silicon oxide layer is formed.

Instead of the silicon substrate 31, a substrate made of a material from which an insertion hole and a groove can be formed such as glass or resin like polycarbonate may be used. Instead of the glass substrate 32, a substrate made of a material that transmits light having a wavelength of an optical signal such as sapphire or quartz may be used. A bonding method of the bonded substrate may be weld bonding, fusion bonding, resin boding, or the like.

<Step S20> Optical Element Mounting Step

The optical element 10 is mounted on the second principal surface 30SB of the fiber holding section 30.

On the second principal surface 30SB, a plurality of bonding electrodes 33 are disposed in predetermined positions in advance. When the external electrode 12 of the optical element 10 is, for example, ultrasonically bonded to the bonding electrodes 33, the light emitting section 11 of the optical element 10 is fixed to a position opposed to the insertion hole H1.

During bonding of the optical element 10, stress is applied to the glass substrate 32 of the fiber holding section 30. However, as shown in FIG. 2, in the fiber holding section 30, the insertion hole H1 and the groove H2 are absent in opposed regions opposed to regions where the bonding electrodes 33 are disposed on the second principal surface 30SB, that is, regions where the external electrode 12 of the optical element 10 is bonded. The regions where the bonding electrodes 33 of the glass substrate 32 are disposed are reinforced because the silicon substrate 31 is present. Accordingly, it is unlikely that the thin glass substrate 32 is broken during the bonding of the optical element 10. The optical module 1 has high reliability because a bonding pressure can be set high when the optical element 10 is, for example, ultrasonically bonded.

<Step S30> Resin Injecting Step

The liquid-like transparent resin 40 before hardening is injected from the groove H2 of the fiber holding section 30. The transparent resin 40 is disposed in the groove H2 and the insertion hole H1.

The transparent resin 40 flows into the insertion hole H1 from a side surface by passing through the groove H2, which is a channel Therefore, air bubbles do not remain in the insertion hole H1.

For the transparent resin 40, any one of various kinds of ultraviolet curing resin having high light transmittance and a predetermined refractive index or ultraviolet curing and thermosetting resin, for example, silicone resin or epoxy resin is used.

For example, the transparent resin 40 is injected into the groove H2 from the opening of the groove H2 of the first principal surface 30SA of the fiber holding section 30. The groove H2 is the narrowest in the connecting section to the insertion hole H1. Conversely, the groove H2 is wide in the side surface 30SS. Accordingly, in a state in which the side surface 30SS of the fiber holding section 30 is faced upward, the transparent resin 40 may be injected into the groove H2 from the side surface opening of the groove H2.

Note that, since the groove H2 of the fiber holding section 30 has the bottom surface, it is possible to effectively prevent mixing of bubbles by injecting the transparent resin 40 to flow along the glass substrate 32 forming the bottom surface.

<Step S40> Optical Fiber Inserting Step

The optical fiber 20 is inserted into the insertion hole H1.

When the resin is injected after the optical fiber 20 is inserted, it is likely that a position in an optical axis direction of the inserted optical fiber 20 moves. In the manufacturing method in the present embodiment, since the optical fiber is inserted after the resin is injected, it is unlikely that the optical fiber moves.

When the optical fiber 20 is inserted into the insertion hole H1 into which the transparent resin 40 is injected, pressure is applied by the transparent resin 40 pushed by the optical fiber 20. Accordingly, it is likely that the glass substrate 32 is broken.

In the manufacturing method in the present embodiment, the pushed-out transparent resin 40 overflows from the opening of the groove 112. Accordingly, when the optical fiber 20 is inserted into the insertion hole H1, it is unlikely that the thin glass substrate 32 is broken by an insertion pressure.

<Step S50> Resin Hardening Step

The transparent resin 40 is hardened. In other words, the transparent resin 40 is irradiated with an ultraviolet ray. A gap between the insertion hole H1 and the optical fiber 20 is extremely small. Accordingly, it is not easy to irradiate the transparent resin 40 in the gap with the ultraviolet ray.

However, the groove H2 connected to the insertion hole H1 is present in the fiber holding section 30. Accordingly, the ultraviolet ray can be efficiently applied to the transparent resin 40 in the insertion hole H1 from at least one of the opening of the groove H2 on the first principal surface 30SA and the opening of the groove H2 on the side surface.

In other words, the groove H2 is effective not only to dispose the transparent resin 40 in the insertion hole H1 but also to apply the ultraviolet ray to the transparent resin 40 in the insertion hole H1.

Note that when the transparent resin 40 is the ultraviolet curing and thermosetting resin, for example, a thermosetting step at 100° C. for one hour is further performed after the ultraviolet ray irradiating step.

Since the step of fixing, with the transparent resin 40, the optical fiber 20 inserted into the insertion hole H1 can be surely performed without breaking the glass substrate 32, it is easy to manufacture the optical module 1.

Figure 8:
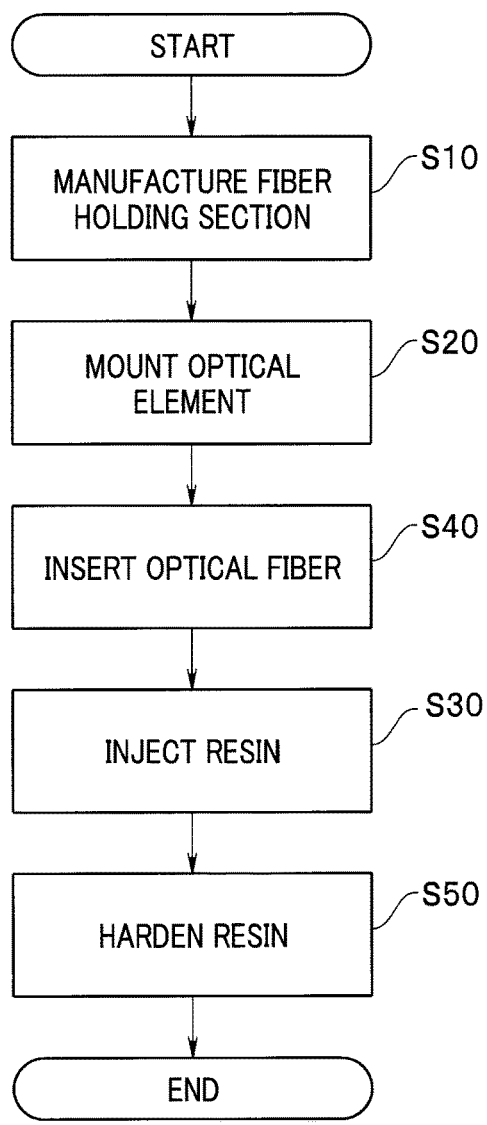
FIG. 8 is a manufacturing flowchart of the optical module in the first embodiment.

Note that, as shown in the flowchart of FIG. 8, step S30 (the resin injecting step) may be performed after step S40 (the optical fiber inserting step).

In this case, in step S30, it is possible to perform the injection of the transparent resin 40 while causing the optical element 10 to emit light and monitoring a light amount of the light guided by the optical fiber 20. Then, it is possible confirm with an increase in the light amount that the transparent resin 40 is filled in a gap between a distal end face of the optical fiber 20 and the glass substrate 32.

Further, in step S40, it is possible to visually confirm that the optical fiber 20 comes into contact with the glass substrate 32. When the optical fiber 20 is inserted, since the transparent resin 40 is not injected into the insertion hole H1, it is possible to insert the optical fiber 20 while checking the insertion hole H1.

<Modifications of the First Embodiment>

Optical modules 1A to 1E in modifications 1 to 5 of the first embodiment are similar to the optical module 1 and have the same effects. Therefore, the components having the same functions are denoted by the same reference numerals and signs and explanation of the components is omitted.

<Modification 1 of the First Embodiment>

Figure 9:
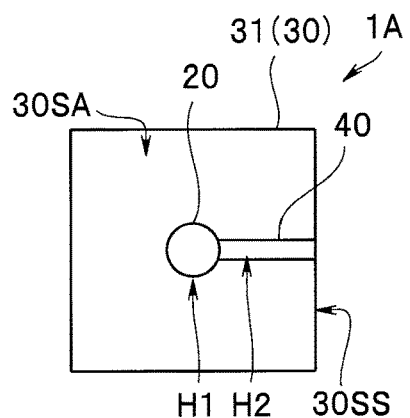
FIG. 9 is a top view of a fiber holding section of an optical module in a modification 1 of the first embodiment.

In the optical module 1A in the modification shown in FIG. 9, the width of the groove H2 of the fiber holding section 30 is fixed. The insertion hole H1 and the groove H2 do not have tapers.

It goes without saying that even the optical module 1A is more easily manufactured, has higher reliability, and has higher transmission efficiency than the conventional optical module without the groove H2.

<Modification 2 of the First Embodiment>

Figure 10:
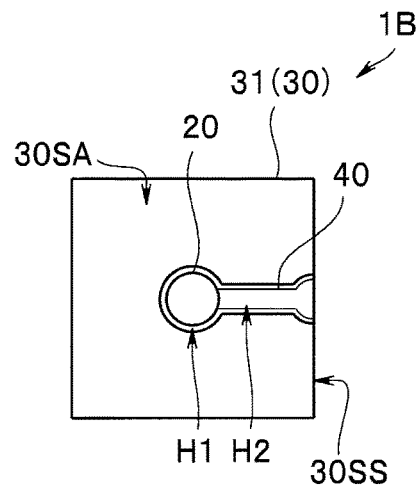
FIG. 10 is a top view of a fiber holding section of an optical module in a modification 2 of the first embodiment.

In the optical module 1B in the modification shown in FIG. 10, a hole, a bottom surface of which is made of a transparent material and a side surface of which is an opening, is present at an end portion of the groove H2 of the fiber holding section 30. The groove H2 has a semicircular shape in which a diameter of an opening on the first principal surface 30SA is larger than the width of the groove H2. In other words, the width of the opening on the first principal surface 30SA of the hole is larger than the width of the groove H2.

In the optical module 1B, as in the optical module 1, it is easy to inject the transparent resin 40 from the opening on the side surface 30SS. Positioning accuracy of the optical fiber 20 is not deteriorated.

<Modification 3 of the First Embodiment>

Figure 11:
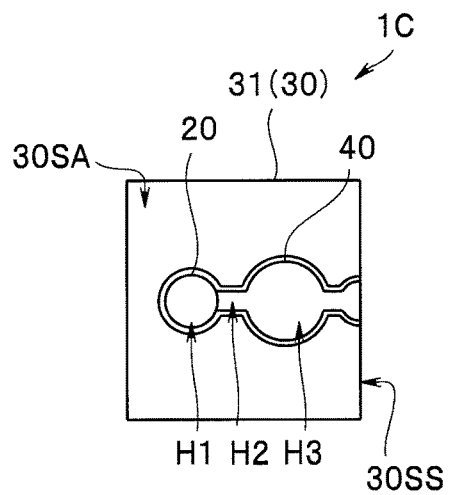
FIG. 11 is a top view of a fiber holding section of an optical module in a modification 3 of the first embodiment.

In the optical module 1C in the modification shown in FIG. 11, an injection hole H3 is present in an intermediate part of the groove H2. In other words, the injection hole H3, an inner diameter of which is larger than the width of the groove H2, is present between the insertion hole H1 of the groove H2 and the opening on the side surface 30SS. Further, a hole, a bottom surface of which is made of a transparent material and a side surface of which is an opening, is present at the end portion of the groove H2. A width of the opening on the first principal surface 30SA of the hole is larger than the width of the groove H2.

For example, when the inner diameter of the insertion hole H1 is 85 µm, the inner diameter of the injection hole H3 is 200 µm and the width of the groove H2 is 50 µm. A width of a portion of the groove H2 in contact with the insertion hole H1 only has to be smaller than the inner diameter of the insertion hole H1 but is preferably 80% or less of the inner diameter of the insertion hole H1 in order to stably hold the optical fiber 20 inserted into the insertion hole H1. The insertion hole H1, the groove H2, and the injection hole H3 do not have tapers but may have tapers. An inner surface shape of the injection hole H3 is not limited to a column and may be a prism.

As explained below, the optical fiber 20 is fixed by the transparent resin 40 of the ultraviolet curing type injected from the injection hole H3. Accordingly, the transparent resin 40 is disposed in the insertion hole H1, the injection hole H3, and the groove H2.

The transparent resin 40 is injected from the bottom surface side toward the first principal surface 30SA using, for example, a micro syringe inserted into the injection hole H3. Accordingly, in the optical module 1C, it is not particularly likely that bubbles are mixed.

Note that the insertion hole H1, the injection hole H3, and the groove H2 of the fiber holding section 30 are bottomed. Accordingly, it is unlikely that the optical element 10 is broken by the micro syringe and the transparent resin 40 spreads to the second principal surface 30SB.

The insertion hole H1, the groove H2, and the injection hole H3 of the fiber holding section 30 are disposed on one straight line. Accordingly, when the optical fiber 20 is inserted into the insertion hole H1, a distal end face position of the optical fiber 20 can be confirmed from the side surface 30SS and, at the same time, an ultraviolet ray can be irradiated from the side surface opening.

<Modification 4 of the First Embodiment>

Figure 12:
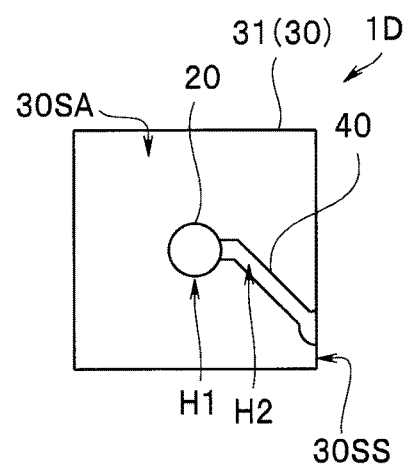
FIG. 12 is a top view of a fiber holding section of an optical module in a modification 4 of the first embodiment.

In the optical module 1D in the modification shown in FIG. 12, a hole, a bottom surface of which is made of a transparent material and a side surface of which is an opening, is present at the end portion of the groove H2. A width of the opening on the first principal surface 30SA of the hole is larger than the width of the groove H2. The groove H2 is not linear and is bent. Although not illustrated, the groove H2 can avoid a region to which the external electrode 12 of the optical element 10 is bonded. The insertion hole H1 and the groove H2 do not have tapers but may have tapers.

<Modification 5 of the First Embodiment>

Figure 13:
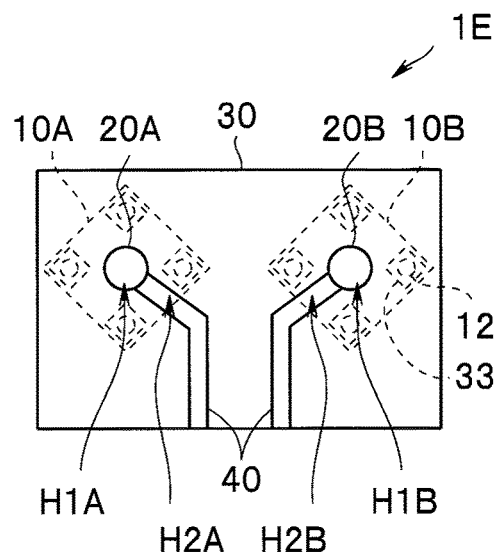
FIG. 13 is a top view of a fiber holding section of an optical module in a modification 5 of the first embodiment.

The optical module 1E in the modification shown in FIG. 13 includes two optical elements 10A and 10B, two optical fibers 20A and 20B, and the fiber holding section 30. Two insertion holes H1A and H1B and two grooves H2A and H2B are present in the fiber holding section 30. The insertion holes H1A and H1B and the grooves H2A and H2B do not have tapers but may have tapers.

The optical fiber 20A inserted into the insertion hole H1A transmits a first optical signal outputted by the optical element 10A. The optical fiber 20B inserted into the insertion hole H1B transmits a second optical signal outputted by the optical element 10B.

The optical module 1E have the effects of the optical module 1 and the like. Further, it goes without saying that the optical module 1E can transmit a larger number of signals than the optical module 1 and the like.

Second Embodiment

An optical module 1F in a second embodiment and optical modules 1G to 1K in modifications of the second embodiment are similar to the optical module 1 and the like and have the same effects. Therefore, the components having the same functions are denoted by the same reference numerals and signs and explanation of the components is omitted.

Figure 14:
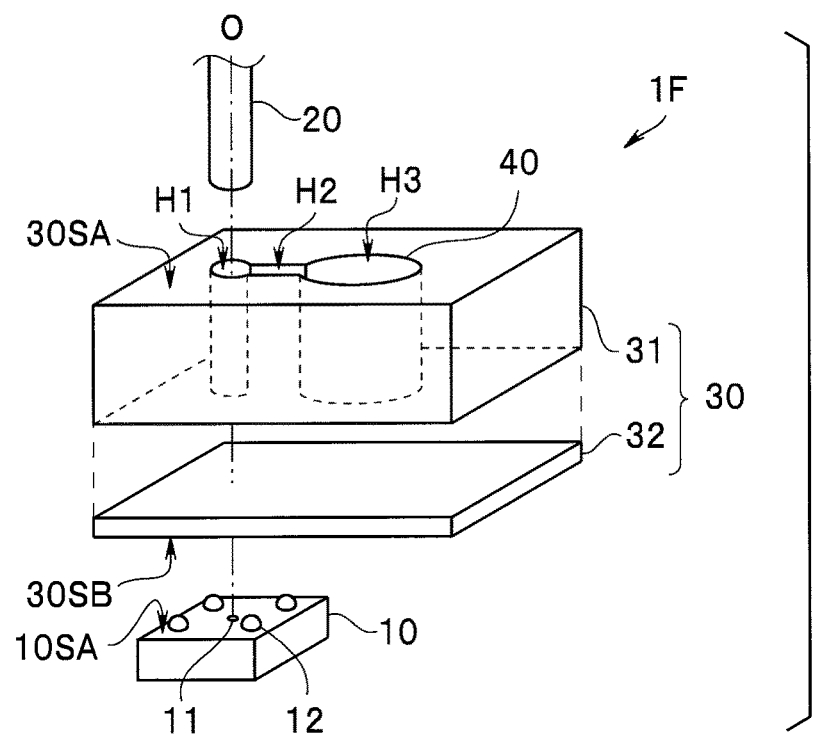
FIG. 14 is an exploded perspective view of an optical module in a second embodiment.
Figure 15:
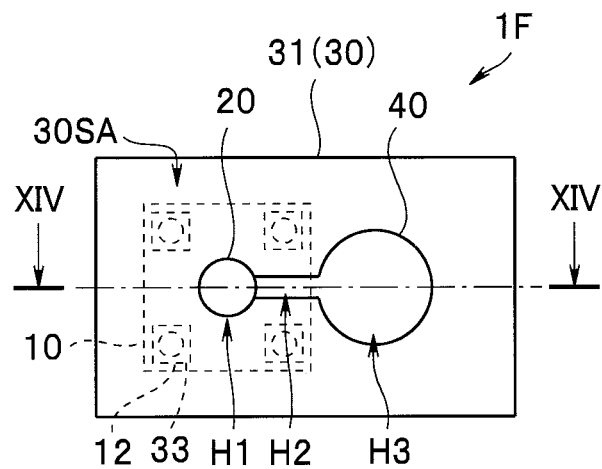
FIG. 15 is a top view of the optical module in the second embodiment.
Figure 16:
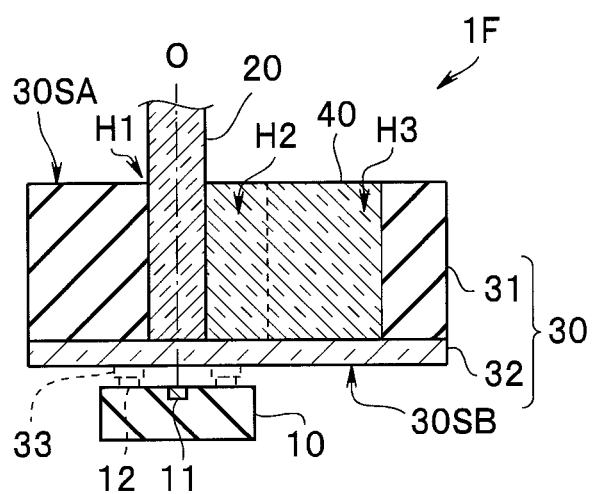
FIG. 16 is a sectional view taken along a line XV-XV of FIG. 15.

On the first principal surface 30SA of the fiber holding section 30 of the optical module 1F in the second embodiment shown in FIG. 14 to FIG. 16, the insertion hole H1, the groove (the slit or the path) H2 connected to the insertion hole H1, and the injection hole H3, an inner diameter of which is larger than the width of the groove H2, connected to the end portion of the groove H2 are present. The groove H2 is not extended to the side surface 30SS. In all of the insertion hole H1, the injection hole H3, and the groove H2, openings are present on the first principal surface 30SA and wall surfaces are formed of silicon. The insertion hole H1, the injection hole H3, and the groove H2 are bottomed and bottom surfaces of the insertion hole H1, the injection hole H3, and the groove H2 are formed of glass.

On the first principal surface 30SA of the fiber holding section 30 of the optical module 1F, not only the opening of the insertion hole H1 but also the opening of the injection hole H3 and the opening of the groove H2 are present. Accordingly, an ultraviolet ray irradiated from above the first principal surface 30SA passes through the transparent resin 40 disposed in the injection hole H3 and the groove H2 to thereby reach the transparent resin 40 in the insertion hole H1. Accordingly, the transparent resin 40 in the insertion hole H1 for fixing the optical fiber 20 can be sufficiently hardened. Further, since the transparent resin 40 flows into the insertion hole H1 by passing through the injection hole H3 and the groove H2, air bubbles do not remain in the transparent resin 40.

The optical module 1F has high reliability and is small in size and has high transmission efficiency and is easily manufactured.

<Modifications of the Second Embodiment>

Optical modules 1G to 1K in modifications 1 to 5 of the second embodiment are similar to the optical module 1F and have the same effects. Therefore, the components having the same functions are denoted by the same reference numerals and signs and explanation of the components is omitted. Note that, in the optical modules 1G to 1K, the insertion hole H1 and the like do not have tapers but may have tapers.

<Modification 1 of the Second Embodiment>

Figure 17:
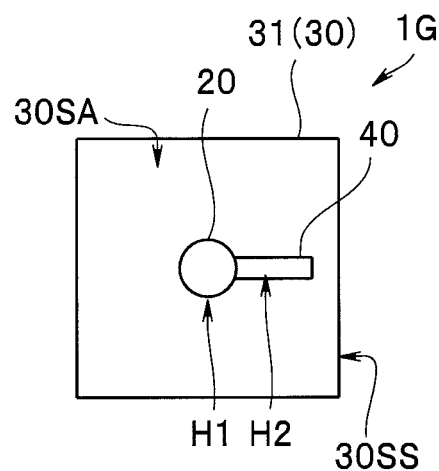
FIG. 17 is a top view of a fiber holding section of an optical module in a modification 1 of the second embodiment.

The groove H2 of the fiber holding section 30 of the optical module 1G in the modification shown in FIG. 17 is not extended to the side surface 30SS. The groove H2, which is linear and the width of which is fixed, does not have an opening on the side surface 30SS.

<Modification 2 of the Second Embodiment>

Figure 18:
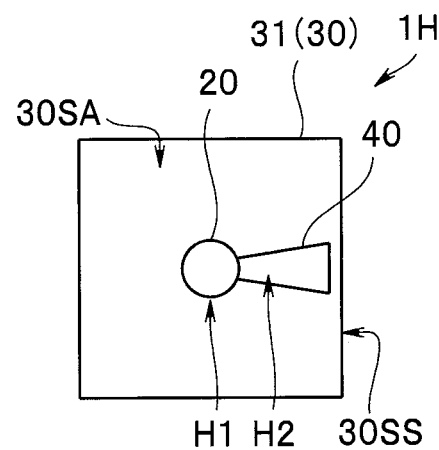
FIG. 18 is a top view of a fiber holding section of an optical module in a modification 2 of the second embodiment.

The groove H2 of the fiber holding section 30 of the optical module 1H in the modification shown in FIG. 18 is not extended to the side surface 30SS. The groove H2 is narrowed toward the insertion hole H1.

<Modification 3 of the Second Embodiment>

Figure 19:
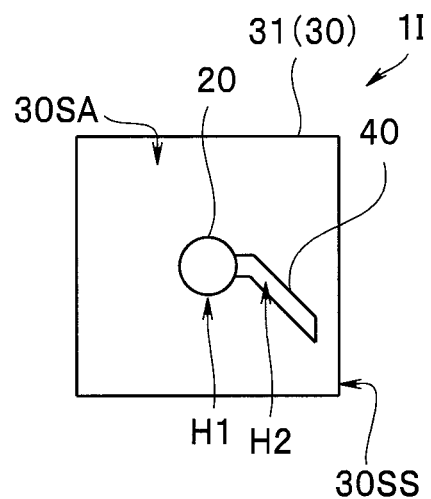
FIG. 19 is a top view of a fiber holding section of an optical module in a modification 3 of the second embodiment.

The groove H2 of the fiber holding section 30 of the optical module 1I in the modification shown in FIG. 19 is bent in the same manner as the optical module 1D. Accordingly, the groove H2 can avoid a region to which the external electrode 12 of the optical element 10 is bonded.

<Modification 4 of the Second Embodiment>

Figure 20:
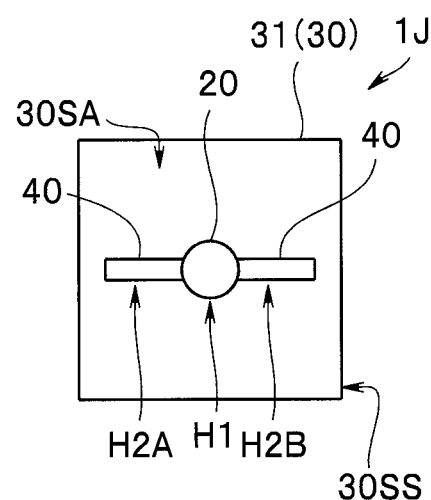
FIG. 20 is a top view of a fiber holding section of an optical module in a modification 4 of the second embodiment.

Two grooves H2A and H2B are present in the fiber holding section 30 of the optical module 1J in the modification shown in FIG. 20. In other words, the groove H2 extended from the insertion hole H1 is not limited to one.

<Modification 5 of the Second Embodiment>

Figure 21:
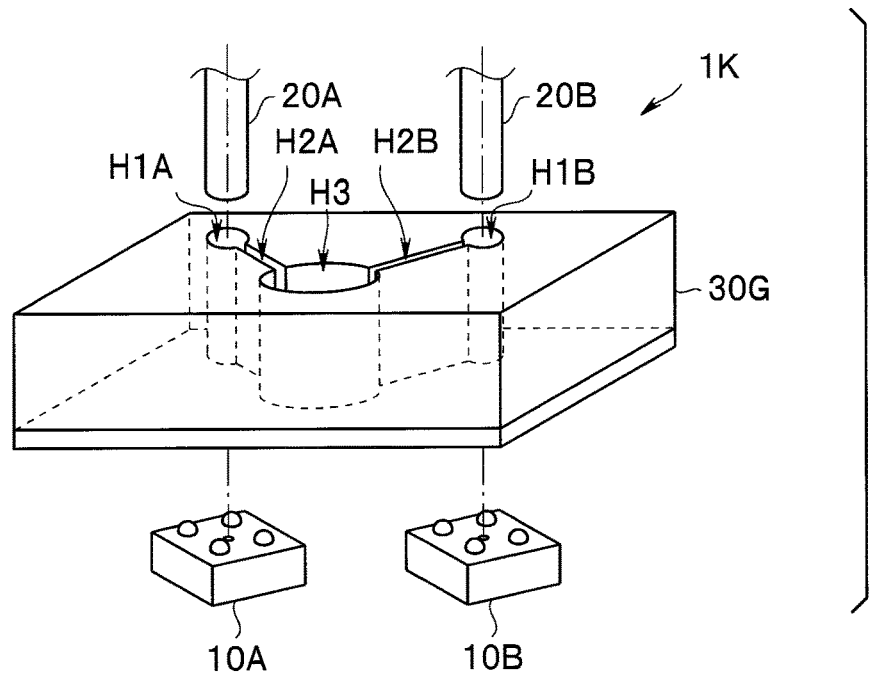
FIG. 21 is an exploded perspective view of an optical module in a modification 5 of the second embodiment.

The optical module 1K in the modification shown in FIG. 21 includes two optical elements 10A and 10B, two optical fibers 20A and 20B, and the fiber holding section 30. Two insertion holes H1A and H1B and two grooves H2A and H2B are present in the fiber holding section 30. The two grooves H2A and H2B are extended to one injection hole H3.

The transparent resin 40 injected into the injection hole H3 is disposed in the insertion holes H1A and H1B by passing through the grooves H2A and H2B. Since the transparent resin 40 can be disposed in the two insertion holes H1A and H1B by one injection work. Therefore, it is easy to manufacture the optical module 1K.

As explained above, the optical module of the present invention may include a plurality of optical fibers.

Note that one optical module may include grooves having different forms. For example, the linear groove shown in FIG. 9 may be extended from the insertion hole H1A and the bending groove shown in FIG. 12 may be extended from the insertion hole H1B.

Third Embodiment

Subsequently, the endoscope 5 in a third embodiment is explained. The endoscope 5 shown in FIG. 22 includes the optical module 1 (1A to 1K) at a distal end portion 9A of an insertion section 9B.

The endoscope 5 includes the insertion section 9B, at the distal end portion 9A of which the image pickup device 2 having a large number of pixels is disposed, an operation section 9C disposed on a proximal end side of the insertion section 9B, and a universal cord 9D extending from the operation section 9C.

An electric signal outputted by the image pickup device 2 is converted into an optical signal by the optical module 1 of the E/O type, converted into an electric signal again by an optical module 1X of the O/E type, an optical element of which is a light receiving element, disposed in the operation section 9C after passing through the optical fiber 20, and transmitted by passing through a metal wire. In other words, in the insertion section 9B having a small diameter, a signal is transmitted by passing through the optical fiber 20.

The electric signal outputted by the image pickup device 2 may be converted into an optical signal by the optical module 1 of the E/O type and, after passing through the optical fiber 20 inserted through the insertion section 9B, the operation section 9C, and the universal cord 9D, converted into an electric signal by the optical module 1X of the O/E type, an optical element of which is a PD, disposed in the processor (not illustrated). The processor performs signal processing for causing a display apparatus, for example, a liquid crystal monitor to display, as an image, the electric signal converted by the optical module 1X of the O/E type.

As explained above, the optical module 1 (1A to 1K) is small in size and has high reliability and high productivity. Accordingly, since the insertion section has a small diameter, the endoscope 5 (5A to 5K) is low-invasive and has high reliability and high productivity.

Note that the optical module 1X is disposed in the operation section 9C where a disposition space is relatively wide. However, the optical module 1X may have the same configuration as the configuration of the optical module 1 and the like of the present invention. The endoscope 5 is a flexible endoscope but may be a rigid endoscope. A use of the endoscope 5 may be a medical use or may be an industrial use. A control signal to the image pickup device 2 may be converted into an optical signal by the optical module 1 disposed in the operation section 9C, and the optical signal may be converted into an electric signal by the optical module 1X disposed in the distal end portion 9A.

Note that the optical module 1 and the like are light emitting elements in which the optical element 10 and the like include the light emitting section 11 that outputs an optical signal. In contrast, even when an optical element of an optical module is a light receiving element such as a photodiode including a light receiving section to which an optical signal is inputted, the optical module has the same effects as the optical module 1 and the like.

In other words, the optical element only has to include a light emitting section that outputs an optical signal or a light receiving section to which an optical signal is inputted and an external electrode connected to the light emitting section or the light reception section.

The present invention is not limited to the embodiments explained above. Various changes, combinations, and applications are possible within a range not departing from the gist of the invention.

What is claimed is:

1. An optical module for endoscope comprising:
   at least one optical element including a light emission circuit that outputs an optical signal or a light reception circuit to which the optical signal is inputted and an external electrode connected to the light emission circuit or the light reception circuit;
   at least one optical fiber for transmitting the optical signal;
   a ferrule including a first principal surface, a second principal surface on an opposite side of the first principal surface, and a side surface orthogonal to the first principal surface, an opening of at least one insertion hole being present on the first principal surface, the insertion hole having a bottom surface made of a transparent material, the optical fiber being inserted into the insertion hole, the external electrode of the optical element being bonded to a bonding electrode of the second principal surface, an opening of a groove connected to the insertion hole being present on the first principal surface, the groove having a bottom surface made of the transparent material; and transparent resin of an ultraviolet curing type or an ultraviolet and thermosetting type disposed in the insertion hole and the groove of the ferrule.

2. The optical module for endoscope according to claim 1, wherein the ferrule is made of silicon, and the insertion hole and the groove have tapers, and openings on the first principal surface of the insertion hole and the groove are larger than bottom surfaces of the insertion hole and the groove.

3. The optical module for endoscope according to claim 1, wherein the groove is extended to the side surface of the ferrule, and the groove includes an opening on the side surface.

4. The optical module for endoscope according to claim 1, wherein the groove is not extended to the side surface of the ferrule.

5. The optical module for endoscope according to claim 1, wherein a width of the groove is smallest in a connecting section to the insertion hole.

6. The optical module for endoscope according to claim 1, wherein an injection hole is present in an intermediate part of the groove, a bottom surface of the injection hole being made of the transparent material, and an inner diameter of the insertion hole is larger than a width of the groove.

7. The optical module for endoscope according to claim 1, wherein a hole is present at an end portion of the groove, a bottom surface of the hole being made of the transparent material and a side surface of the hole being an opening, and a width of the hole is larger than a width of the groove.

8. An endoscope comprising an optical module for endoscope, the optical module for endoscope including:

at least one optical element including a light emission circuit that outputs an optical signal or a light reception circuit to which the optical signal is inputted and an external electrode connected to the light emission circuit or the light reception circuit;

at least one optical fiber for transmitting the optical signal;

a ferrule including a first principal surface, a second principal surface on an opposite side of the first principal surface, and a side surface orthogonal to the first principal surface, an opening of at least one insertion hole being present on the first principal surface, the insertion hole having a bottom surface made of a transparent material, the optical fiber being inserted into the insertion hole, the external electrode of the optical element being bonded to a bonding electrode of the second principal surface, an opening of a groove connected to the insertion hole being present on the first principal surface, the groove having a bottom surface made of the transparent material; and transparent resin of an ultraviolet curing type or an ultraviolet and thermosetting type disposed in the insertion hole and the groove of the ferrule.

9. A manufacturing method of an optical module for endoscope comprising:

manufacturing a ferrule including a first principal surface, a second principal surface on an opposite side of the first principal surface, and a side surface orthogonal to the first principal surface, an opening of an insertion hole being present on the first principal surface, the insertion hole having a bottom surface made of a transparent material, an opening of a groove connected to the insertion hole being present on the first principal surface, the groove having a bottom surface made of the transparent material;

bonding, to a bonding electrode on the second principal surface of the ferrule, an external electrode of an optical element including a light emission circuit or a light reception circuit and the external electrode connected to the light emission circuit or the light reception circuit;

inserting an optical fiber for transmitting an optical signal into the insertion hole of the ferrule;

injecting the transparent resin not hardened yet into the groove and disposing the unhardened transparent resin in the groove and the insertion hole; and hardening the transparent resin with ultraviolet ray irradiation or the ultraviolet ray irradiation and heating.

* * * * *